(12) United States Patent
Adell

(10) Patent No.: US 10,390,912 B1
(45) Date of Patent: Aug. 27, 2019

(54) THERMOFORMING AIDS AND METHODS

(71) Applicant: Loren S. Adell, Sunnyvale, TX (US)

(72) Inventor: Loren S. Adell, Sunnyvale, TX (US)

(73) Assignees: Loren S. Adell, Sunnyvale, TX (US);
Michael Adell, Sunnyvale, TX (US)

( * ) Notice: Subject to any disclaimer, the term of this patent is extended or adjusted under 35 U.S.C. 154(b) by 981 days.

(21) Appl. No.: 14/703,475

(22) Filed: May 4, 2015

(51) Int. Cl.
*A61C 9/00* (2006.01)

(52) U.S. Cl.
CPC ..................................... *A61C 9/00* (2013.01)

(58) Field of Classification Search
CPC ......... B29C 51/00; B29C 51/02; B29C 51/04; B29C 51/10; B29C 51/14; B29C 51/16; B29C 51/18; B29C 51/26
See application file for complete search history.

(56) References Cited

U.S. PATENT DOCUMENTS

| | | | | |
|---|---|---|---|---|
| 4,838,973 A | * | 6/1989 | Mentzer | B29C 37/0025 156/212 |
| 5,648,031 A | * | 7/1997 | Sturtevant | B05D 5/02 264/134 |
| 9,526,591 B2 | | 12/2016 | Adell | |
| 2009/0324901 A1 | * | 12/2009 | Hashiba | B29C 51/002 428/195.1 |
| 2012/0211928 A1 | * | 8/2012 | Takai | B29C 51/10 264/553 |
| 2014/0113092 A1 | * | 4/2014 | Doll | B65D 19/385 428/36.5 |
| 2014/0154477 A1 | * | 6/2014 | Chu | B65D 65/44 428/178 |
| 2015/0360411 A1 | * | 12/2015 | Saelen | B29C 51/36 428/174 |
| 2017/0057152 A1 | * | 3/2017 | Mizoguchi | B29C 51/12 |
| 2017/0165897 A1 | * | 6/2017 | Saelen | B29C 51/087 |

* cited by examiner

*Primary Examiner* — Nahida Sultana
(74) *Attorney, Agent, or Firm* — George L. Boller

(57) ABSTRACT

A thermoforming aid for use in creating a thermoformed impression of an object such as a dental arch. The thermoforming aid has a thermoformable sheet which has inherent tendency to curl when unsupported, and a curl-resistant element which prevents the thermoformable sheet from curling. The thermoforming aid makes a person's task of placing a sheet of thermoformable material, especially a very thin sheet having an inherent tendency to curl, in proper position in a thermoforming machine less difficult and time-consuming.

13 Claims, 5 Drawing Sheets

THERMOFORMING AIDS AND METHODS

FIELD OF THE INVENTION

This invention relates generally to thermoforming, and in particular to thermoforming aids for use in thermoforming machines and to methods of using such aids in thermoforming machines.

CROSS-REFERENCE TO A RELATED APPLICATION

Applicant's pending application Ser. No. 13/200,004, filed Sep. 9, 2011, now U.S. Pat. No. 9,526,591, issued Dec. 27, 2016, is incorporated herein in its entirety by reference although its priority is not claimed.

BACKGROUND OF THE INVENTION

Thermoforming is a process for creating various products by heating thermoformable material and causing the heated material to form onto at least a portion of an object and create an impression of at least a portion of the object in the thermoformable material. The thermoformable material may be a sheet which is placed in a thermoforming machine which when operated, heats the thermoformable sheet and causes the heated thermoformable sheet to form onto at least a portion of the object and create an impression of at least a portion of the object in the heated thermoformable sheet. A vacuum may be used to draw the heated sheet into intimate contact with the object. The impression created in the sheet is retained when the sheet cools.

Thermoforming machines are commonly used in dentists' offices and dental laboratories for creating thermoformed impressions of objects used in the practice of dentistry which includes not only general dentistry but also dental specialties such as orthodontia for example. Application Ser. No. 13/200,004 discloses a method of thermoforming a thin sheet of thermoformable material onto a dental arch model.

A typical practice for using a thermoforming machine involves manually placing a perimeter margin of a thin sheet of thermoformable material on an open-center platen of the machine and closing an open-center cover onto the perimeter margin of the sheet to hold the sheet in proper position for thermoforming onto an object such as a dental arch model. The thermoforming machine comprises a base on which the object is placed. With a sheet of thermoformable material held between the platen and the cover, the sheet is heated and begins to droop. With the platen and the closed cover holding the perimeter margin of the sheet, they are moved downward to drape the drooping sheet over the object while cooperating with the base to form a closed space within which the object is disposed with the sheet draped over it. Vacuum is then drawn within the closed space through multiple passages in the base to cause the draped sheet to more intimately form onto the object. After that, the vacuum is turned off and the sheet is allowed to cool. Upon completion of cooling, the formed sheet is removed from the object, retaining an impression of the object.

When the object is a model of a dental arch, or portion of such a model, an impression of teeth of the model, and any devices which may be affixed to the model, are captured in fixed form in the thermoformed material. As described in application Ser. No. 13/200,004, devices such as orthodontic brackets which are releasably mounted on the model may be captured in the thermoformed material and separate from the model along with the thermoformed material during removal of the material from the model.

Thinness of a sheet of thermoformable material may be an important factor in the quality of a resulting impression because it can affect the ability of the thermoform material to form around an object with a desired degree of precision. In general, a very thin sheet can be formed around an object with greater precision that can a thicker sheet.

SUMMARY OF THE DISCLOSURE OF THE INVENTION

A very thin sheet of certain thermoformable materials has an inherent tendency to curl. That tendency can make proper placement of the sheet on the platen by the user of a thermoforming machine difficult and time consuming.

Briefly, this disclosure introduces novel thermoforming aids and methods for using those aids in thermoforming machines to create impressions of at least portions of objects, a dental arch model being one example of such an object.

These aids make a person's task of placing a sheet of thermoformable material, especially a very thin sheet having an inherent tendency to curl, in proper position in a thermoforming machine less difficult and time-consuming.

The foregoing summary is accompanied by further detail of the disclosure presented in the Detailed Description below with reference to the following drawings which are part of the disclosure.

DETAILED DESCRIPTION

Figure 1:
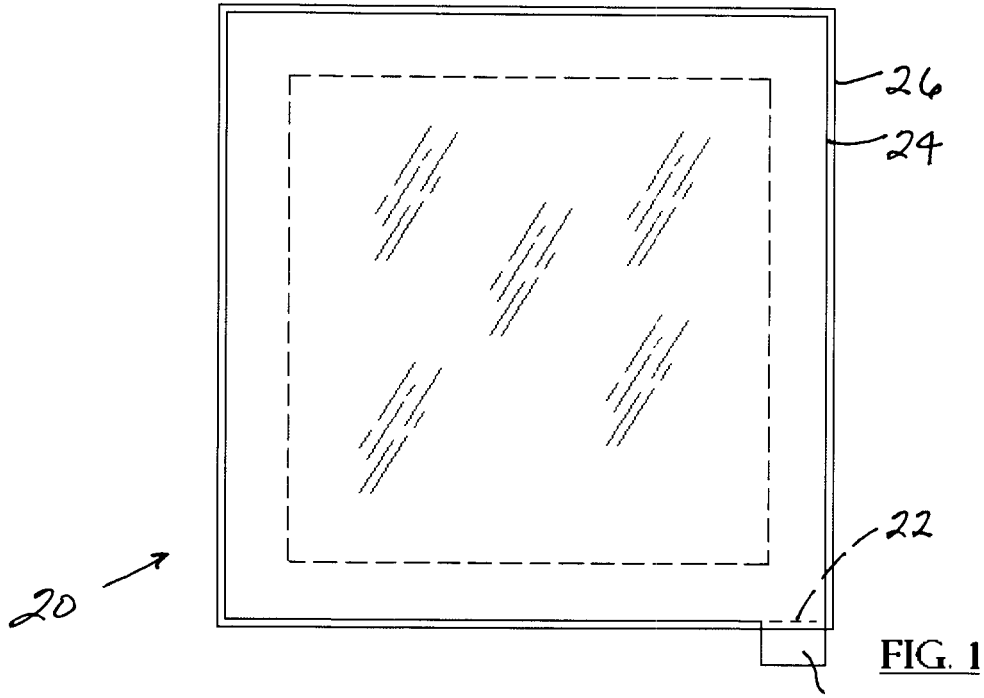
FIG. 1 is a top plan view of a first example of a thermoforming aid for use in a thermoforming machine.
Figure 2:
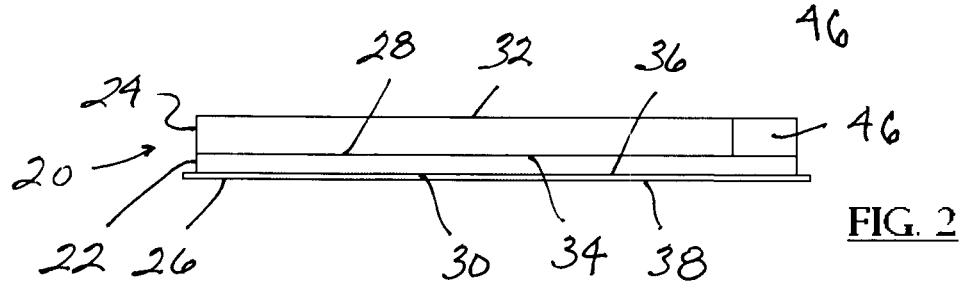
FIG. 2 is front elevation view of the thermoforming aid of FIG. 1.

FIG. 1 and FIG. 2 show a first example of a thermoforming aid 20 for use in a thermoforming machine. The rectangular shape shown in FIG. 1 is representative of one particular shape for use in a machine having a rectangular platen, but other shapes, such as circular or oval, would be appropriate for platens of other shapes. For clarity of illustration, the thickness shown in FIG. 2 is greatly exaggerated when compared with the length and width shown in FIG. 1.

Thermoforming aid 20 comprises a rectangular thermoformable sheet 22, a curl-resistant element 24, and a release cover 26. Thermoformable sheet 22 has an upper surface 28 and a lower surface 30. Curl-resistant element 24 has an upper surface 32 and a lower surface 34. Release cover 26 has an upper surface 36 and a lower surface 38. Lower surface 34 of curl-resistant element 24 is disposed in full surface-to-surface contact with upper surface 28 of thermoformable sheet 22. Lower surface 30 of thermoformable sheet 22 is disposed in surface-to-surface contact with upper surface 36 of release cover 26.

Thermoformable sheet 22 has a thickness, as measured between its upper surface 28 and its lower surface 30, selected to obtain a desired characteristic, such as degree of precision, in a finished impression of an object onto which it is ultimately formed. Certain thermoformable materials in sufficiently thin sheet form possess an inherent tendency to curl when unsupported. Curling has different degrees ranging from partial curling of a perimeter edge of a sheet which doesn't form a full convolution, to curling of a perimeter margin into one or more convolutions of a roll.

Curl-resistant element 24 possesses resistance to curling which, through its surface-to-surface contact with thermoformable sheet 22, prevents thermoformable sheet 22 from curling as it otherwise would during placement by itself on a platen of a thermoforming machine without a curl-resistant element to keep it from curling. The description of element 24 being curl-resistant should not be construed to imply that it must necessarily be flat and rigid and keep the thermoformable sheet flat. Indeed, element 24 may be a thin sheet of material which, as a whole, can flex or warp to a limited extent without its perimeter margin curling.

Figure 3:
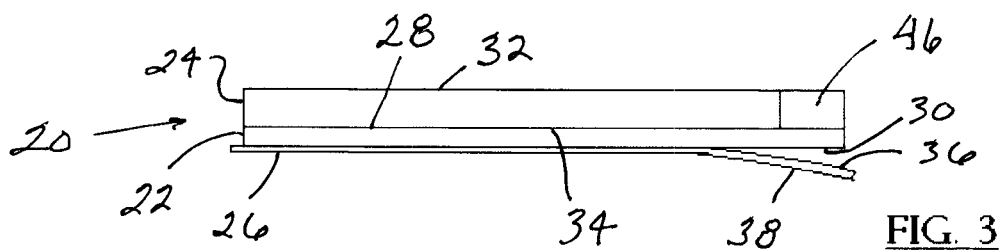
FIG. 3 is front elevation view as in FIG. 2, but showing a beginning of an initial step of removing a first element of the thermoforming aid for enabling the thermoforming aid to be placed in a thermoforming machine.
Figure 4:
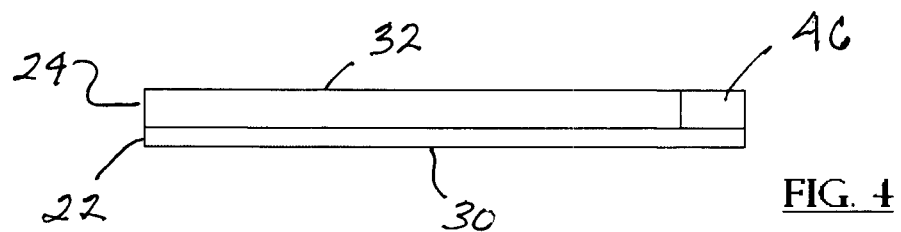
FIG. 4 is front elevation view as in FIG. 3, but with the first element removed.

In preparation for using thermoforming aid 20, release cover 26 is removed. Release cover 26 has a perimeter margin, at least a portion of which extends beyond the perimeter margin of thermoformable sheet 22. In the disclosed embodiment, the complete perimeter margin of release cover 26 extends beyond the perimeter margin of thermoformable sheet 22 to enable a portion of the perimeter margin of release cover 26 to be partially separated from sheet 22 as suggested by FIG. 3 and then gripped between a person's thumb and forefinger and peeled completely off sheet 22, leaving thermoforming aid 20 as shown in FIG. 4.

Removal of release cover 26 exposes a material on lower surface 30 of thermoformable sheet 22 which gives it some degree of tenacity, as will be further explained hereinafter. The exposed material extends completely around the perimeter margin of sheet 22, leaving a center zone free of adhesive.

Figure 5:
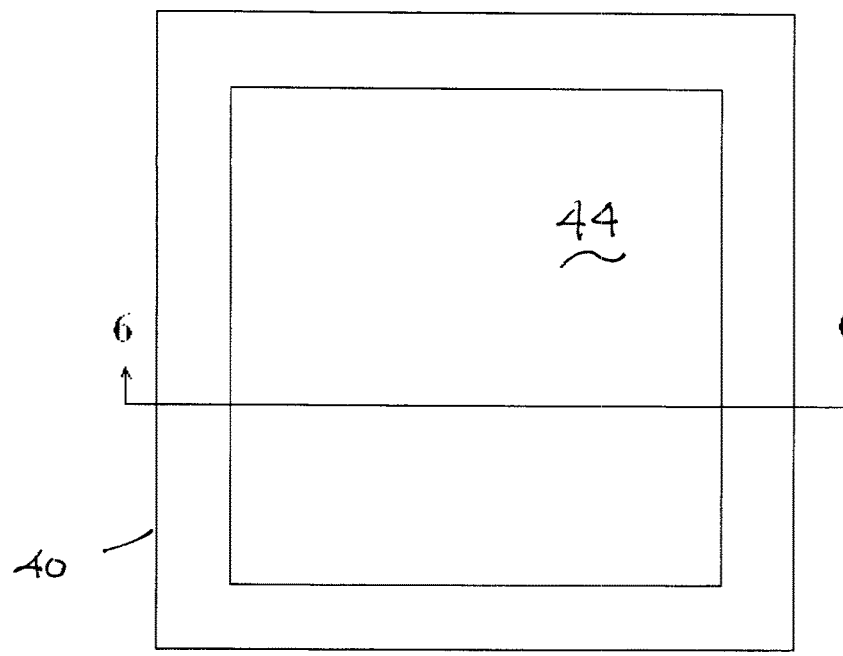
FIG. 5 is a top plan view of a platen of a thermoforming machine.
Figure 6:
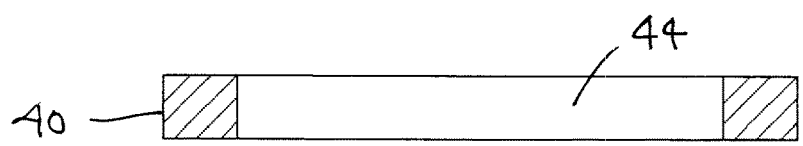
FIG. 6 is a cross section view in the direction of arrows 6-6 in FIG. 5.
Figure 11:
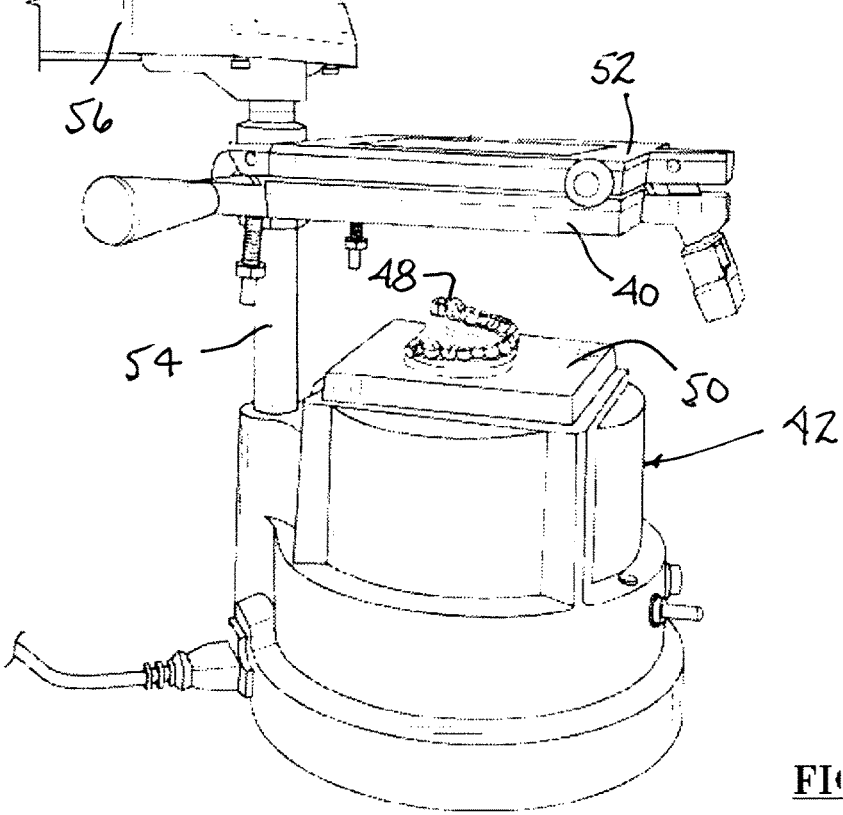
FIG. 11 is a perspective view of a thermoforming machine showing the dental arch model placed on a base of the machine.

FIG. 5 shows a top plan view of a platen 40 of a thermoforming machine 42, an example of which is shown in FIG. 11. Platen 40 has a rectangular shape which surrounds an open rectangular center 44 as also seen in FIG. 6.

Figure 7:
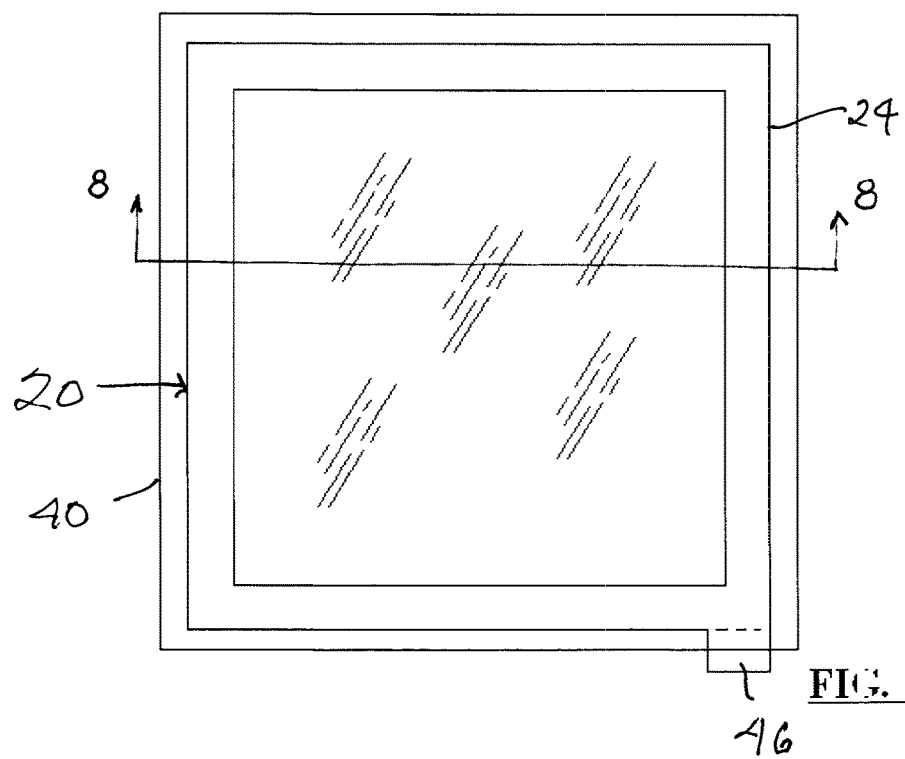
FIG. 7 is a top plan view showing the thermoforming aid of FIG. 4 having been placed on the platen of FIG. 5.

FIG. 7 shows thermoforming aid 20 placed on platen 40 after release cover 26 has been removed. The material on surface 30 of sheet 22 which is exposed by removal of release cover 26 may be an adhesive which endows sheet 22 with sufficient tenacity to be held fast in the flat position in which it is placed on the flat top surface of platen 40 while allowing it to be pulled off the platen after thermoforming.

Curl-resistant element 24 completely covers thermoformable sheet 22 to place the latter's entire upper surface 28 in surface-to-surface contact with the former's lower surface 34. Element 24 has a perimeter margin at least a portion of which extends beyond the perimeter margin of sheet 22, and which in the disclosed embodiment comprises a tab 46 at one corner.

Figure 8:
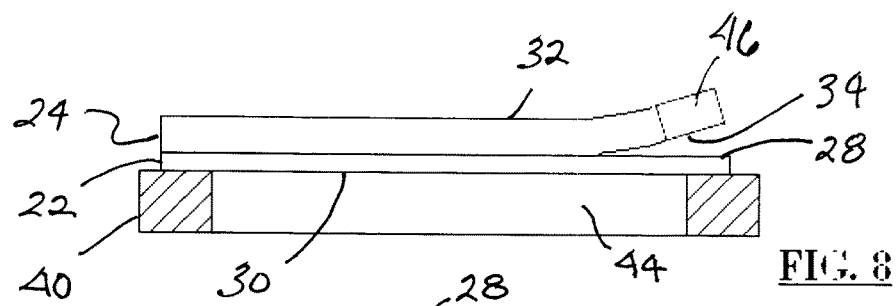
FIG. 8 is a view in the direction of arrows 8-8 in FIG. 7 showing a beginning of a step of removing a second element from the thermoforming aid.
Figure 9:
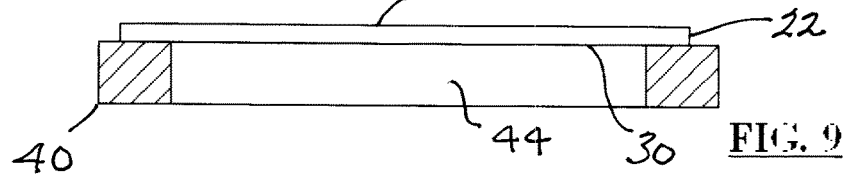
FIG. 9 is view as in FIG. 8 but showing the second element removed.

As suggested by FIG. 8, tab 46 provides a gripping portion of element 24 which can be gripped between a person's thumb and forefinger and pulled upward to peel element 24 off thermoformable sheet 22 while the tenacity of the sheet to platen 40 is sufficient to keep the sheet in place on platen 40 as shown in FIG. 9. A certain degree of care in peeling element 24 off sheet 22 may be appropriate depending on materials, thicknesses, and tenacity of the margin of thermoforming aid 20 to the platen because the adherence of sheet 22 to the platen is intended to be only temporary, not permanent, so as to allow the margin to be conveniently removed from the platen after thermoforming has been completed. If one hand is peeling element 24 too rapidly or too forcefully without digits of the other hand aiding to hold down a portion which has yet to be peeled off, a portion of sheet 22 may be inadvertently pulled off the platen. Consequently, because the adherence of sheet 22 to the platen is intended only to temporarily constrain the sheet against sliding on and separating from the platen until element 24 has been completely peeled off, it is generally preferred that element 24 be slowly peeled off sheet 22 using thumb and finger of one hand while one or more digits of the other hand are pressing down on portions of the perimeter margin of element 24 which have yet to be peeled off.

Figure 10:
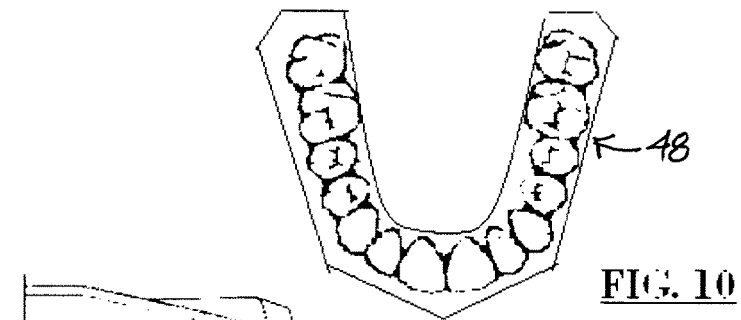
FIG. 10 is a top plan view of a full dental arch model.

A dental arch model 48, shown by itself in FIG. 10, is also shown in FIG. 11 placed on a base 50 of thermoforming machine 42.

Figure 12:
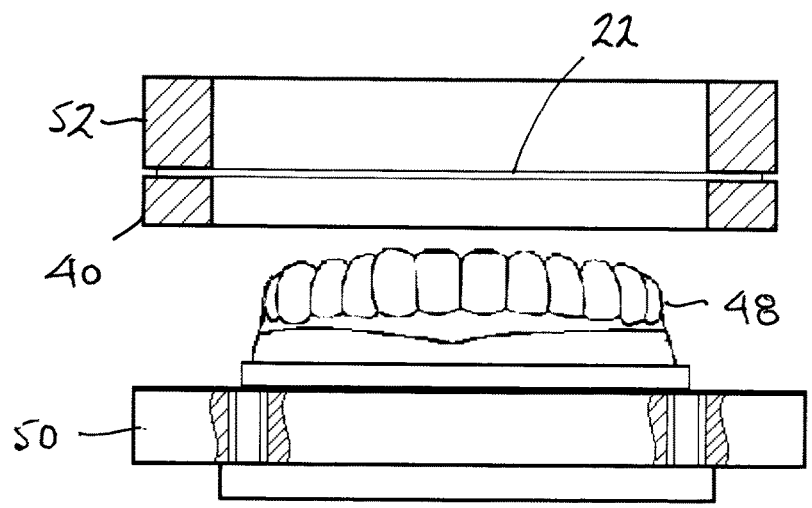
FIGS. 12-14 show a sequence of steps performed by the thermoforming machine during a thermoforming operation.
Figure 13:
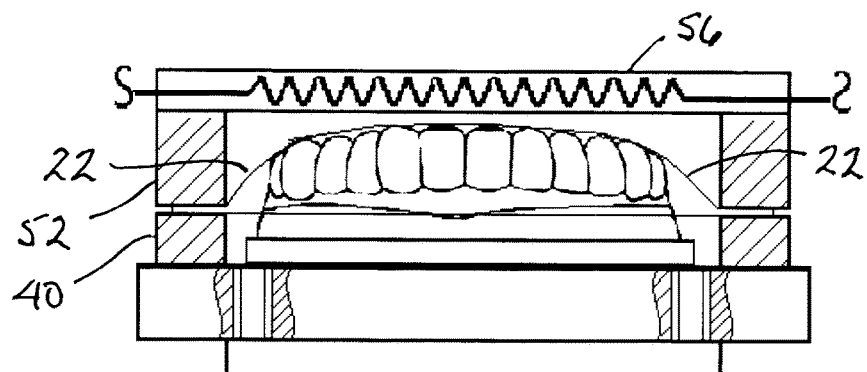
Figure 14:
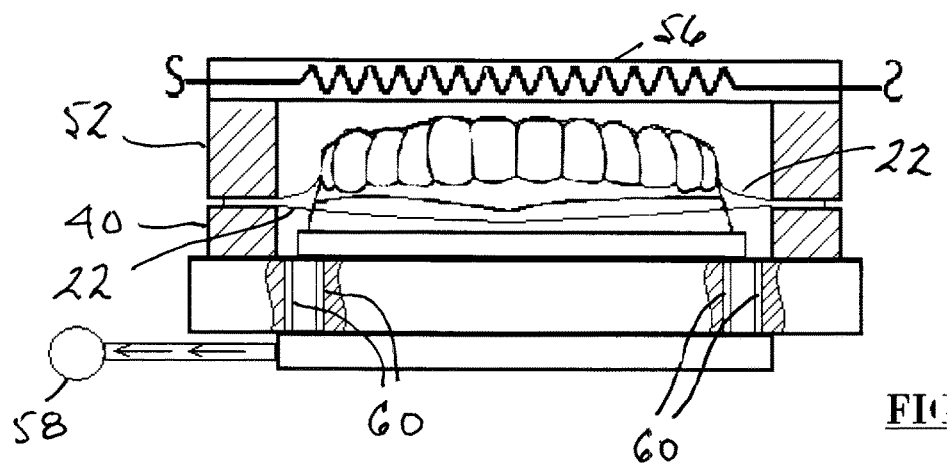

FIGS. 12-14 illustrate further steps in a thermoforming process for creating an impression of dental arch model 48 in sheet 22.

With the perimeter margin of sheet 22 disposed on platen 40 as has been explained, a cover 52 is closed onto the perimeter margin of the sheet as in FIG. 11. Both platen 40 and cover 52 can move up and down on an upright post 54. At the top of post 54 is a heater 56 which can turn horizontally on post 54. Heater 56 is swung from the position shown in FIG. 11 to overlie sheet 22 and with sheet 22 held between platen 40 and cover 52, they are moved from the position shown in FIG. 11 to the one shown in FIG. 12. Heater 56 is operated to begin heating the sheet and softening it while its perimeter margin continues to be held between the platen and cover. After sufficient softening of the sheet, the platen and cover are moved downward to drape the drooping sheet 22 over model 48 as in FIG. 13.

When platen 40 is brought into contact with base 50, a closed space containing model 48 with sheet 22 draped over it is created by base 50, platen 40, and the softened sheet 22. A pump 58 is then operated, as in FIG. 14, to draw vacuum within the closed space through multiple passages 60 in base 50, causing the draped sheet 22 to intimately form onto model 48. The size of sheet 22 is large enough to cover the cusps, lingual, and labial surface of the teeth and the gum line in this particular example. After that, pump 58 is turned off and sheet 22 is allowed to cool. Upon completion of cooling, the formed sheet is removed from the model, retaining an impression of the model.

The impression may in some instances be further processed and/or put to further uses as described in application Ser. No. 13/200,004.

Figure 15:
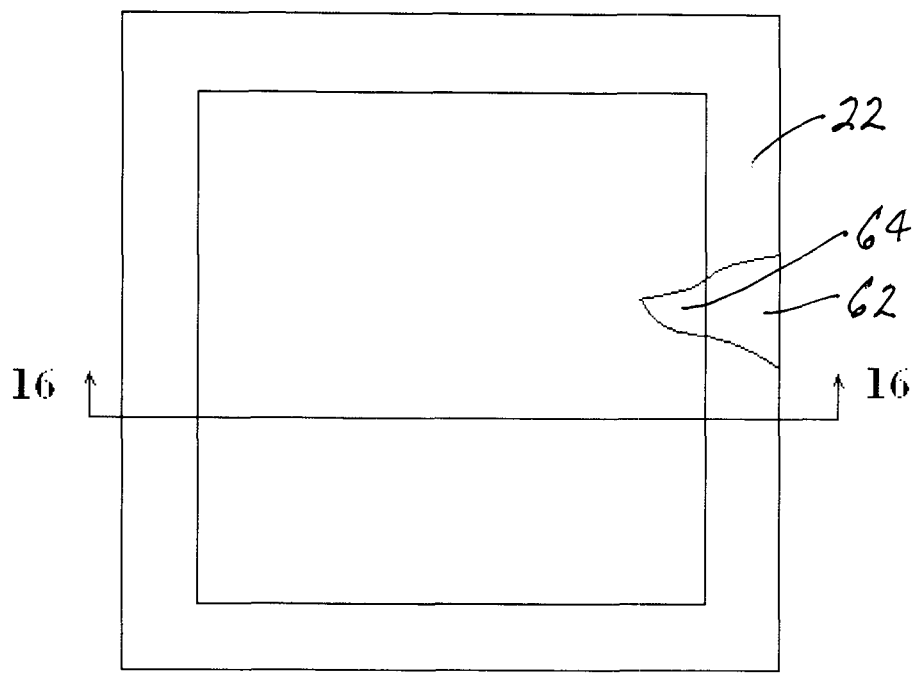
FIG. 15 is a top plan view of a second example of a thermoforming aid for use in a thermoforming machine.
Figure 16:
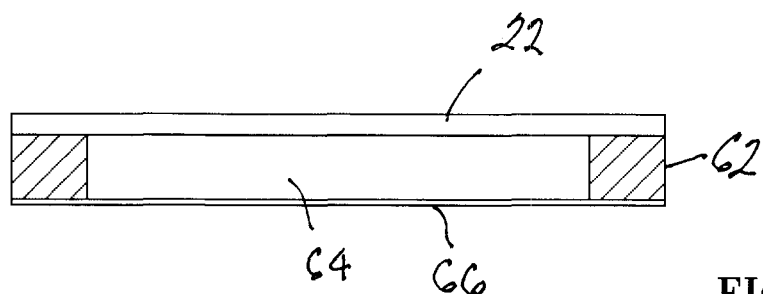
FIG. 16 is a cross section view in the direction of arrows 16-16 in FIG. 15.
Figure 17:
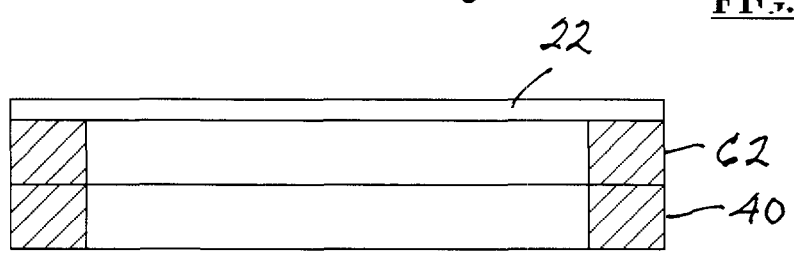
FIG. 17 is a view showing the example of FIG. 16 in place on a thermoforming machine.

FIG. 15 and FIG. 16 show a second example of a thermoforming aid for use in a thermoforming machine. This example comprises a thermoformable sheet 22 and a curl-resistant element 62 having an open center 64. An upper surface of element 62 has full surface-to-surface contact with the entire perimeter margin of the lower surface of sheet 22. Element 62 has a flat lower surface which is treated with an adhesive which when exposed by removal of a release cover 66, provides some degree of adherence when placed on the platen. Hence, this second example differs from the first in that the curl-resistant element remains in place when the thermoforming machine is operated. FIG. 17 shows this example in place on a platen 40 of a thermoforming machine.

Examples of thermoformable materials which, in sufficiently thin sheet form, have an inherent tendency to curl include starches, gelatins, and polyvinyl alcohol. Those materials are dissolvable in water and can be dissolved when placed in a person's mouth as described in application Ser. No. 13/200,004. One specific example of thermoforming aid 20 comprises a starch sheet 22 having a thickness of approximately 0.004 inch and a polyester sheet of approximately 0.010 inch thickness as curl-resistant element 24.

The property of an embodiment to adhere to a platen can be provided by other than an adhesive applied to sheet 22 as in the first example or to curl-resistant element 62 as in the second example. Certain thermoformable materials and curl-resistant materials can adhere to a platen by static electricity which is imparted during a lamination process which is used in the manufacture of thermoforming aid 20 and/or surface friction of either the material which is placed on the platen and/or the platen itself. Certain platens have a groove in their upper surfaces surrounding their open centers. A rubber-based gasket, or equivalent, is disposed in the groove with the upper surface of the gasket substantially flush with the upper surface of the platen. The material of thermoforming aid 20 which is placed on such a gasket has a characteristic which when placed on the gasket possesses its own surface friction which allows surface friction of the gasket to hold the thermoformable sheet in place.

The two examples may be manufactured by a lamination process in which the sheet and the curl-resistant element are laminated by rollers. Pressure of the rollers applied to the materials being laminated can be sufficient to cause the laminates to remain in releasable surface-to-surface contact without use of adhesive. Alternately they can be laminated together using a release adhesive.

What is claimed is:

1. A method of using a thermoforming aid to form a thermoformable sheet onto an object to create an impression of the object in the thermoformable sheet, the method comprising:
   placing a thermoforming aid which comprises a thermoformable sheet having an inherent tendency to curl and a curl-resistant element which is in surface-to-surface contact with a surface of the thermoformable sheet to prevent the thermoformable sheet from curling, on an open-center platen of a thermoforming machine by adhering a perimeter margin of a lower surface of one of the thermoformable sheet and the curl-resistant element to the platen;
   placing an object underneath the thermoformable sheet; and
   operating, the thermoforming machine to heat the thermoformable sheet and cause the heated thermoformable sheet to form onto an object and create an impression of at least a portion of the object in the thermoformable sheet,
   in which adhering a perimeter margin of a lower surface of one of the thermoformable sheet and the curl-resistant element to the platen comprises adhering a perimeter margin of a lower surface of the thermoformable sheet to the platen, and
   in which the adhering the perimeter margin of a lower surface of the thermoformable sheet to the platen comprises adhesively adhering a perimeter margin of a lower surface of the thermoformable sheet to the platen using adhesive which is on the perimeter margin of the lower surface of the thermoformable sheet.

2. A method as set forth in claim 1 further comprising removing a release cover releasably covering the adhesive to expose the adhesive for adhesively adhering the perimeter margin of the lower surface of the thermoformable sheet to the platen.

3. A method as set forth in claim 2 further comprising removing the curl-resistant element from the thermoformable sheet after adhesively adhering the perimeter margin of the lower surface of the thermoformable sheet to the platen.

4. A method as set forth in claim 3 in which removing the curl-resistant element from the thermoformable sheet comprises gripping a portion of the curl-resistant element which extends beyond the perimeter margin of the thermoformable sheet and using, the gripped portion to pull the curl-resistant element off the thermoformable sheet.

5. A method of using a thermoforming aid to form a thermoformable sheet onto an object to create an impression of the object in the thermoformable sheet, the method comprising:
   placing a thermoforming aid which comprises a thermoformable sheet having an inherent tendency to curl and a curl-resistant element which is in surface-to-surface contact with a surface of the thermoformable sheet to prevent the thermoformable sheet from curling, on an open-center platen of a thermoforming machine by adhering a perimeter margin of a lower surface of one of the thermoformable sheet and the curl-resistant element to the platen;
   placing an object underneath the thermoformable sheet; and
   operating the thermoforming machine to heat the thermoformable sheet and cause the heated thermoformable sheet to form onto an object and create an impression of at least a portion of the object in the thermoformable sheet,
   in which adhering a perimeter margin of a lower surface of the curl-resistant element to the platen comprises adhesively adhering a perimeter margin of a lower surface of the curl-resistant element to the platen using adhesive which is on the perimeter margin of the lower surface of the curl-resistant element.

6. A method of using a thermoforming aid to form a thermoformable sheet onto an object to create an impression of the object in the thermoformable sheet, the method comprising:
   placing a thermoforming aid which comprises a thermoformable sheet having an inherent tendency to curl and a curl-resistant element which is in surface-to-surface contact with a surface of the thermoformable sheet to prevent the thermoformable sheet from curling, on an open-center platen of a thermoforming machine by adhering a perimeter margin of a lower surface of one of the thermoformable sheet and the curl-resistant element to the platen;

placing an object underneath the thermoformable sheet; and operating the thermoforming machine to heat the thermoformable sheet and cause the heated thermoformable sheet to form onto an object and create an impression of at least a portion of the object in the thermoformable sheet, in which placing an object underneath the thermoformable sheet comprises placing a dental arch model underneath the thermoformable sheet; and operating the thermoforming machine to heat the thermoformable sheet and cause the heated thermoformable sheet to form onto the dental arch model and create an impression of at least a portion of the dental arch model in the thermoformable sheet.

7. A method as set forth in claim 6 comprising placing the impression of at least a portion of the dental arch model in the thermoformable sheet in a person's dental arch.

8. A method as set forth in claim 7 further comprising causing the impression of at least a portion of the dental arch model in the thermoformable sheet to dissolve in the person's dental arch.

9. A method as set forth in claim 6 which adhering a perimeter margin of a lower surface of one of the thermoformable sheet and the curl-resistant element to the platen comprises adhering a perimeter margin of a lower surface of the thermoformable sheet to the platen.

10. A method as set forth in claim 9 in which adhering a perimeter margin of a lower surface of the thermoformable sheet to the platen comprises adhesively adhering a perimeter margin of a lower surface of the thermoformable sheet to the platen using adhesive which is on the perimeter margin of the lower surface of the thermoformable sheet.

11. A method as set forth in claim 10 further comprising removing a release cover releasably covering the adhesive to expose the adhesive for adhesively adhering the perimeter margin of the lower surface of the thermoformable sheet to the platen.

12. A method as set forth in claim 11 further comprising removing the curl-resistant element from the thermoformable sheet after adhesively adhering the perimeter margin of the lower surface of the thermoformable sheet to the platen.

13. A method as set forth in claim 12 which removing the curl-resistant element from the thermoformable sheet comprises gripping a portion of the curl-resistant element which extends beyond the perimeter margin of the thermoformable sheet and using the gripped portion to pull the curl-resistant element off the thermoformable sheet.

* * * * *